United States Patent
Good et al.

(10) Patent No.: US 6,553,356 B1
(45) Date of Patent: Apr. 22, 2003

(54) MULTI-VIEW COMPUTER-ASSISTED DIAGNOSIS

(75) Inventors: Walter F Good, Pittsburgh, PA (US); David Gur, Pittsburgh, PA (US); Glenn S. Maitz, Pittsburgh, PA (US); Yuan-Hsiang Chang, Pittsburgh, PA (US); Bin Zheng, Pittsburgh, PA (US); Xiao Hui Wang, Pittsburgh, PA (US)

(73) Assignee: University of Pittsburgh - of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 09/471,334

(22) Filed: Dec. 23, 1999

(51) Int. Cl.[7] .............................................. G06F 15/18
(52) U.S. Cl. ........................................ 706/15; 382/156
(58) Field of Search ................................ 382/128, 224, 382/156; 600/431, 407, 549, 455; 378/37; 706/15; 530/350

(56) References Cited

U.S. PATENT DOCUMENTS

| | | | | |
|---|---|---|---|---|
| 5,615,243 A | * | 3/1997 | Chang et al. | 378/37 |
| 5,627,907 A | * | 5/1997 | Gur et al. | 382/132 |
| 5,838,815 A | * | 11/1998 | Gur et al. | 382/128 |
| 5,872,859 A | * | 2/1999 | Gur et al. | 382/128 |
| 5,987,346 A | * | 11/1999 | Benaron et al. | 600/407 |
| 6,067,372 A | * | 5/2000 | Gur et al. | 378/128 |
| 6,246,901 B1 | * | 6/2001 | Benaron | 600/431 |
| 6,278,793 B1 | * | 8/2001 | Gur et al. | 378/128 |

OTHER PUBLICATIONS

Yin et al. "Computerized Detection of Masses in Digital Mammograms: Analysis of Bilateral Subtraction Images", Med. Phys. 18 (5), Sep./Oct. 1991—Am. Assoc. Phys. Med. pp. 955–963.

Fujita et al. "Automated Detection of Masses and Clustered Microcalcifications on Mammograms", SPIE vol. 2434—3/95, pp. 682–692.

Hand et al. "Computer Screening of Xeromammograms: A Technique for Defining Suspicious Areas of the Breast", Computers and Biomedical Research 12, pp. 445–460 (1979).

Ng et al., "Automated Detection and Classification of Breast Tumors", Computers and Biomedical Research 25, pp. 218–237 (1992).

Brzakovic et al. An Approach to Automated Detection of Tumors in Mammograms), IEEE Transactions on Medical Imaging, vol. 9. No. 3, Sep. 1990, pp. 233–241.

Ackerman et al. "Breast Lesion Classification by Computer and Xeroradiograph", Classification of Xeroradiographs—No. 4,—Oct. 1972, ppp. 1025–1035.

Lai et al, "On Techniques for Detecting Circumscribed Masses in Mammograms", IEEE Transactions on Medical Imaging, vol. 8. No. 4—Dec. 1989, pp. 377–386.

Wald et al. "UKCCCR Multicentre Randomised Controlled Trial of One and Two View Mammography in Breast Cancer Screening", BMI vol. 311 Nov. 4, 1995, pp. 1193, 1189.

(List continued on next page.)

*Primary Examiner*—John Follansbee
*Assistant Examiner*—Michael B. Holmes
(74) *Attorney, Agent, or Firm*—Pillsbury Winthrop LLP

(57) ABSTRACT

Abnormal regions in living tissue are detected by obtaining images from different views of the living tissue; performing single-image CAD of each image to determine suspected abnormal regions depicted in the image; and combining measurements of the suspected abnormal regions in each image to determine whether a suspected abnormal region is an abnormal region. The living tissue may be a human breast and the abnormal region may be a mass in the breast. Ipsilateral mammographic views of the breast, a craniocaudal view, and a mediolateral oblique view may be used. Features which are relatively invariant or behave predictably with respect to breast compression are extracted using the single-image CAD and then combined.

52 Claims, 9 Drawing Sheets

OTHER PUBLICATIONS

Maitz et al., "Preliminary Clinical Evaluation of a High-Resolution Telemammography System", Investigative Radiology, Apr. 1997, vol. 32, No. 4.

Zheng et al., "Computer–Aided Detection of Clustered Microcalcifications in Digitized Mammograms", Acad Radiol–Association of University of Radiologists, 1995—2:655–662.

Zheng et al. "Computerized Detection of Masses in Digitized Mammograms Using Single–Image Segmentation and a Multilayer Topographic Feature Analysis", Acad Radiol–Association of University Radiologists, 1995—2:959–966.

Swann et al., "Localization of Occult Breast Lesions: Practical Solutions to Problems of Triangulation", vol. 163, No. 2, Radiology pp. 577–579.

Folio et al., "Nipple Arc Localization", Appl. Radiol. Dec. 17–19, 1994.

Muir et al. "Oblique–View Mammography: Adequacy for Screening", Radiology—1984.

Nishikawa et al., "PHYSICS—Digital Image Processing: Computer–aided Diagnosis"—In Joint sponsorship with the American Association of Physicists in Medicine—Friday—Room N137 (L–6).

Harris et al., "Medical Imaging 1993: PACS Design and Evaluation", SPIE—The International Society for Optical Engineering, vol. 1899 PACS Design and Evaluation (1993) pp. 46–52.

Giger et al., "Investigation of Methods for the Computerized Detection and Analysis of Mammographic Masses", SPIE—The International Society for Optical Engineering, vol. 1233 Medical Imaging IV: Image Processing (1990) pp. 183–184.

Good et al., "Joint Photographic Experts Group (JPEG) Compatible Data Compression of Mammograms", Journal of Digital Imaging, vol. 7, No. 3 (Aug. 1994—pp. 123–132.

Kegelmeyer, Jr. "Computer Detection of Stellate Lesions in Mammograms", SPIE vol. 1660 Biomedical Image Processing and Three–Dimensional Microscopy (1992) pp. 446–454.

Kegelmeyer et al. "Computer–Aided Mammographic Screening for Spiculated Lesions", Radiology 1994—191:331–337.

* cited by examiner

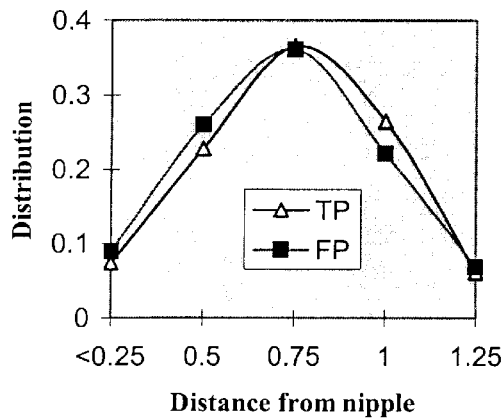
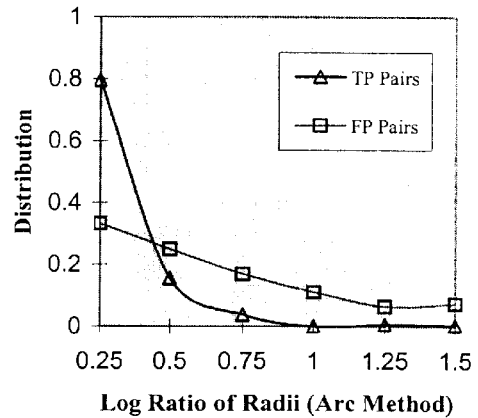
*FIG. 6A*  *FIG. 6B*
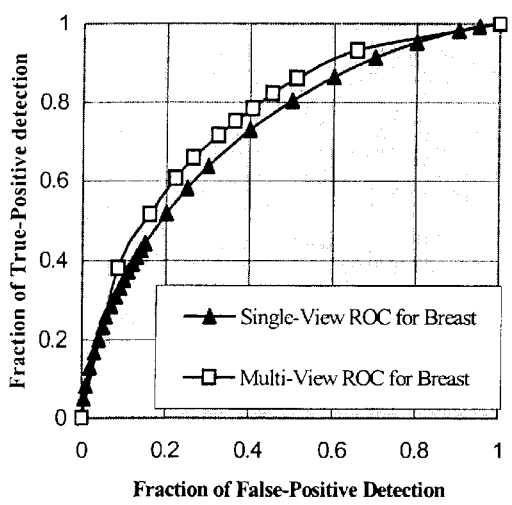
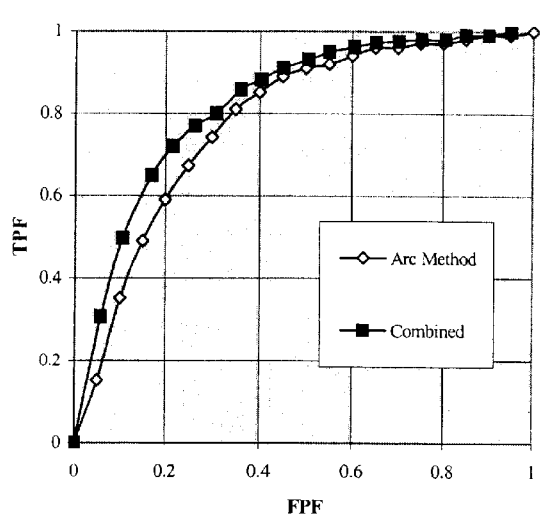
*FIG. 7*  *FIG. 8*

MULTI-VIEW COMPUTER-ASSISTED DIAGNOSIS

STATEMENT REGARDING FEDERALLY SPONSORED RESEARCH OR DEVELOPMENT

This work is sponsored in part by grants CA62800, CA77850 and CA82912 from the National Cancer Institute and LM06236 from the National Library of Medicine, National Institutes of Health, USA.

RESERVATION OF COPYRIGHT

This patent document contains material which is subject to copyright protection. The copyright owner has no objection to the facsimile reproduction by anyone of the patent document or the patent disclosure, as it appears in the U.S. Patent and Trademark Office patent files or records after the granting of a patent, but otherwise reserves all copyrights whatsoever.

BACKGROUND OF THE INVENTION

1. Field of Invention

This invention relates to computerized detection of abnormal anatomical regions depicted in radiographs.

2. Background

Detection and analysis of target objects in digital images are useful and important tasks. For example, detection and diagnosis of abnormal anatomical regions in radiographs, such as masses and microcalcifications in women's breast radiographs (mammograms), are among the most important and difficult tasks performed by radiologists.

Breast cancer is a leading cause of premature death in women over forty years old. Evidence shows that early detection, diagnosis and treatment of breast cancer significantly improves the chances of survival, reducing breast cancer morbidity and mortality. Many methods for early detection of breast cancer have been studied and tested, among them mammography. To date, mammography has proven to be the most cost effective means of providing useful information to diagnosticians regarding abnormal features in the breast and potential risks of developing breast cancer in large populations. The American Cancer Society currently recommends the use of periodic mammography and screening of asymptomatic women over the age of forty with annual examinations after the age of fifty. Mammograms may eventually constitute one of the highest volume X-ray images routinely interpreted by radiologists.

Between thirty and fifty percent of breast cancers detected radiographically demonstrate clustered microcalcifications on mammograms, and between sixty and eighty percent of breast cancers reveal microcalcifications upon microscopic examination. Therefore, any increase in the detection of clustered microcalcifications by mammography may lead to further improvements in its efficiency in the detection of early breast cancer.

Currently, acceptable standards of clinical care are that biopsies are typically performed on five to ten women for each cancer removed. With this high biopsy rate is the reasonable assurance that most mammographically detectable early cancers will be resected. However, reducing the biopsy rate without adversely affecting health is desirable. Accordingly, given the large amount of overlap between the characteristics of benign and malignant lesions which appear in mammograms, computer-aided detection and/or diagnosis (CAD) of abnormalities may have a great impact on clinical care.

At present, mammogram readings are performed visually by mammographic experts, that is, physicians and radiologists. Unfortunately, visual reading of mammograms has two major disadvantages. First, it is often possible to miss the breast cancer in its early stages. This is because, unlike many other cancers, there is as yet no clear way to detect premalignant changes in the breast. This results partly from the relative inaccessibility of breast tissue. A second disadvantage of visual reading of mammograms is that these readings are labor intensive, time consuming, and subjective. Also, multiple readings of a single mammogram may be necessary in order to increase the reliability of the diagnosis.

Therefore, it would be advantageous and useful to have CAD systems to help radiologists and physicians obtain quicker, more consistent, and more precise results when performing visual readings of mammograms. Such CAD systems would aid in cancer detection and improve the efficiency and accuracy of large-scale screening.

During the past twenty years, an ever-increasing number of CAD systems for mammography have been developed and tested in an attempt to increase diagnostic accuracy and improve the efficacy and efficiency of mammographic interpretations. Current CAD schemes for mass detection typically can be partitioned into three stages. The first stage identifies suspicious regions using either single image segmentation or bilateral image subtraction; the second stage calculates a feature vector for each of these suspicious regions; and the third stage classifies regions based on some type of decision mechanism applied to feature vectors. Regions which are ultimately classified as positive by the above process can be marked on a copy of the original image for presentation to a radiologist or for use in other analysis.

Recent reports on advances in CAD applied to mass detection indicate that there are some generalizations that can be made about performance limitations of current methods.

In order to achieve a high true-positive detection rate (i.e., sensitivity greater than 90%), all of these schemes report a relatively large false-positive detection rate, even when testing a limited image database. It is not uncommon to produce a false-positive detection rate of one region per image for clustered microcalcifications and two false-positive detections per image for masses. Previous attempts to improve early CAD schemes have employed many different techniques, but none of these efforts have been able to reduce the false positive rate to acceptable levels.

It is widely believed that current performance of CAD for mass detection is significantly less than that of radiologists, given the same task, though quantitative comparisons are difficult because radiologists rarely read single images without supplementary information. To directly compare radiologists' performance with current CAD would require that radiologists be restricted to evaluating limited regions-of-interest on mammograms, in assessing the likelihood of a mass in the region.

SUMMARY OF THE INVENTION

In recent years, despite considerable effort by many groups, the rate of improvement in CAD performance has slowed to the point that performance statistics of the better systems seem to be approaching an asymptote. This performance level, which is largely independent of the specifics of implementation (e.g., neural networks, Bayesian networks or rule based systems), is believed to be well below the potential performance of CAD. The inventors of the present invention believe that a possible reason for this may be that essentially all current CAD implementations apply traditional paradigms of signal processing and pattern recognition to detect features in individual images, and it is probable that most of the relevant physical features, in single-views, have been identified and exploited to some extent. Whatever information remains untapped in single-views is either very elusive (i.e., difficult to program), at a higher level of abstraction, or has only a small potential impact on performance.

In contrast to CAD, mammographers routinely insist on concurrently reading multiple images (at least two of each breast) in evaluating cases. Apparently, a significant part of their decision process requires a synergistic interaction of multiple components of information, as opposed to evaluating each separately and then combining individual decisions. The degree to which each component of image information independently. affects the performance of radiologists, and potentially of CAD, is not known. A limited number of studies have shown that single-view mammography leads to a higher rate of recall, and results in a failure to detect 11% to 25% of cancers than would have been detected using multiple views. These observations, along with the fact that mammographers insist on comparing all views that are available, strongly suggests that they derive useful gains in performance from this.

Ipsilateral pairs of mammograms (i.e., two views of the same breast taken at some oblique angle) contain spatial information about a single breast. However, because the process of acquiring each image requires that the breast be compressed in a direction orthogonal to the image plane (flattened on the image detector), each image of the pair represents a different distortion of the breast tissue. Although it is not feasible to geometrically reconstruct a three dimensional model of the breast from this data, it is possible to derive certain kinds of information by comparing features between views. For example, if a mass appears in one view, it should appear in the second view as well, or there should at least be sufficient ambiguity in the second view to explain its absence. Although the exact location of a feature in the second view will be unknown, there are constraints on where it might appear based on its position in the first image and the geometric effects of breast compression. Many kinds of image features (e.g., location, texture, degree of spiculation, and integrated density difference) tend to be relatively invariant, or at least behave predictably, with respect to breast compression.

In one aspect, this invention is a method of detecting an abnormal region in living tissue. The method includes obtaining images from a different views of the living tissue; performing single-image CAD of each image to determine suspected abnormal regions depicted in the image; and combining measurements of the suspected abnormal regions in each image to determine whether a suspected abnormal region is an abnormal region.

In preferred embodiments, the living tissue is a human breast, the abnormal region is a mass in the breast, and the obtaining comprises obtaining ipsilateral mammographic views of the breast, preferably a craniocaudal view of the breast and a mediolateral oblique view of the breast.

In some embodiments, the single-image CAD of each image produces a feature vector for each of the various suspicious regions depicted in the images. In some preferred embodiments, the features are relatively invariant or behave predictably with respect to breast compression. The features may include one or more of a radial distance of the suspicious region from the nipple; a length of region projection parallel to the nipple axis line; an integrated contrast difference; a size of the suspicious region; and a measure of complexity of the region boundary.

In some embodiments, the combining of measurements comprises evaluating combinations of suspected abnormal regions from each view; and producing a single multi-view measurement for reach suspected abnormal region based on the measurements of each region from each view. In some embodiments, the multi-view measurement is defined to be the absolute value of the logarithm of the ratio of the corresponding single-image measurements. In some embodiments, the result of the combining is used to train the single-image CAD.

In another aspect, this invention is a method of detecting a mass in a human breast. The method includes obtaining ipsilateral mammographic views of the breast; for each image, performing CAD of the image to determine suspected masses depicted in the image; and combining measurements of the suspected masses in each image to determine whether a suspected abnormal region is a mass. In some embodiments, one image is from a craniocaudal view of the breast and the other image is from the mediolateral oblique view of the breast.

In some embodiments, the CAD of each image produces a feature vector of various suspicious regions depicted in the images. The features are preferably relatively invariant or behave predictably with respect to breast compression.

BRIEF DESCRIPTION OF THE DRAWINGS

The above and other objects, features, and advantages of the present invention are further described in the detailed description which follows, with reference to the drawings by way of non-limiting exemplary embodiments of the present invention, wherein like reference numerals represent similar parts of the present invention throughout the several views and wherein

FIGS. 6A–10 depict results of a study of the application of this invention to particular cases.

DETAILED DESCRIPTION OF THE PRESENTLY PREFERRED EXEMPLARY EMBODIMENTS

System Configuration and Implementation

Figure 1:
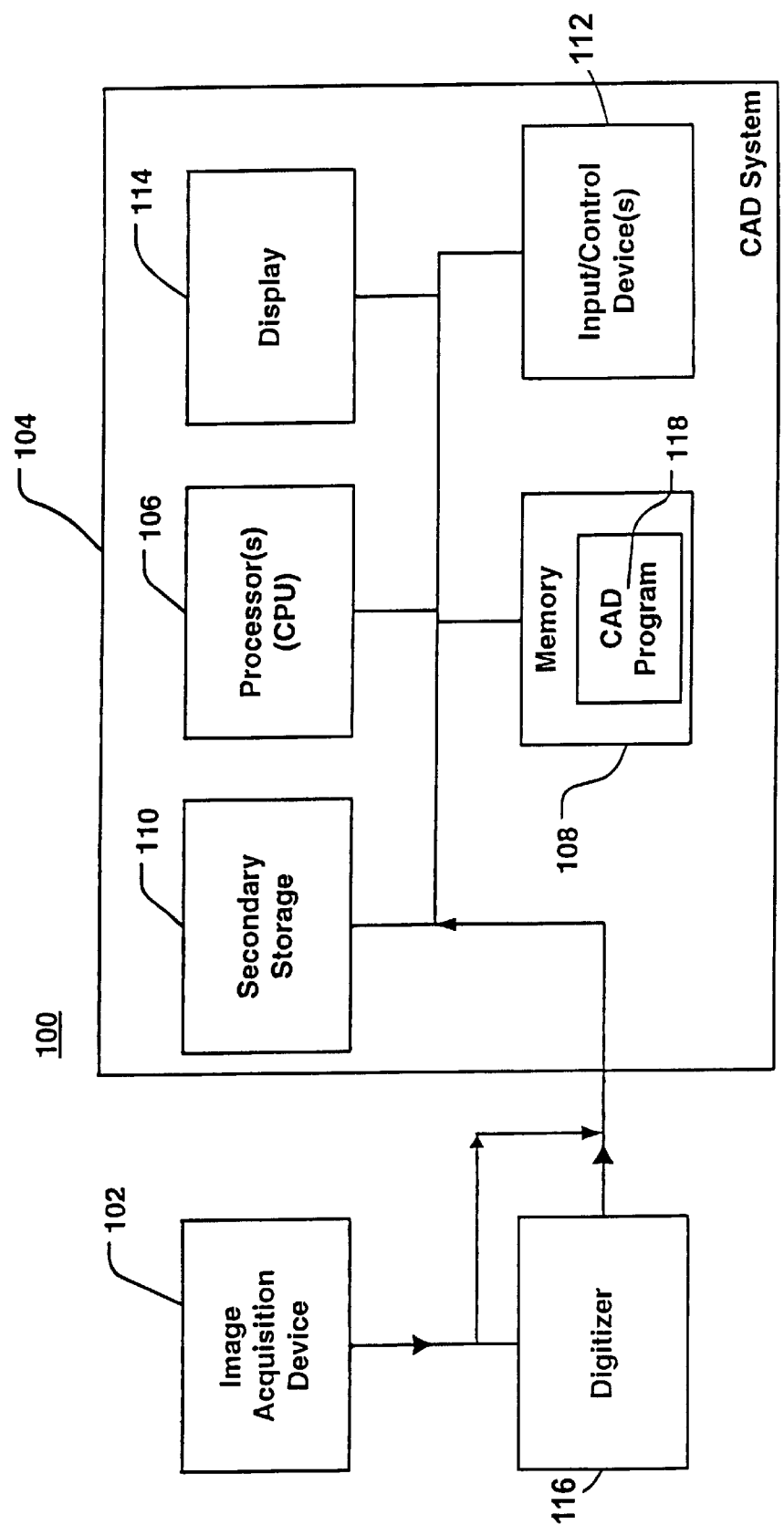
FIG. 1 depicts a typical computer system according to an embodiment of the present invention.

An embodiment of the present invention has been implemented using a system 100 as shown in FIG. 1, wherein an imaging or image acquisition device 102, such as an X-ray mammography device, is connected directly or indirectly to a computer-based CAD system 104 in order to provide the CAD system 104 with image data. The CAD system 104 has at least one central processor (CPU) 106 and a random access memory (RAM) 108. Associated with the CAD system 104 is secondary storage 110, such as, for example, optical disks, hard disks, etc., for storing programs and image data obtained from the imaging device 102. Connected to the computer system 104 are various input and control devices 112, such as, e.g., a keyboard and a mouse. A display 114 is connected to the computer system 104 to display commands, images, and other information produced by the computer system 104. Various enhanced co-processor chips may be installed into the CAD system 104 to work in conjunction with the CPU 106 in order to increase the processing power of the computer. An image digitizer 116 is connected either directly or indirectly to the CAD system 104 in order to provide it with digital image data of the images produced by the imaging device 102. The image digitizer 116 may be integral with the image acquisition device 102 or it may be separate therefrom.

In operation, the imaging device 102 acquires images of the appropriate anatomical area or part of a human body. In some preferred embodiments, the imaging device 102 is a radiographic or X-ray imaging device capable of producing X-ray mammograms with a resolution of at least 500×500 pixels. These mammograms can be from any view appropriate for detection of abnormalities. In preferred embodiments, the imaging device 102 is capable of obtaining ipsilateral mammographic views. The imaging device 102 can generate a direct digital image or provide a mechanism to digitize films. The imaging device 102 may have a separate computer system (not shown) to control its operations for producing radiographs.

The CAD system 104 is connected directly or indirectly to the imaging device 102 in order to obtain, store, and analyze the images produced by the imaging device 102. If the imaging device 102 does not produce digital images, then the digitizer 116, capable of digitizing an image produced by the imaging device 102, can be used to provide digital images to the CAD system 104.

Because of the high resolution required in order to evaluate digital radiographs, typically, the secondary storage 110 is a high capacity storage device, and the display 114 is able to display digital radiographic images at a resolution sufficient to enable and assist in analysis and diagnosis.

In the presently preferred embodiments (at the time this application is being written), a SUN Sparcstation is used as the CAD system 104. The secondary storage device 110 is either an eight millimeter magnetic tape (for example, 3M eight mm data tape) or an optical disk (for example, Laser-Memory DEC-702 rewritable optical disk, available from Pioneer Communications of America, Upper Saddle River, N.J.). The display 114 is a 21-inch Sun color monitor with a screen resolution of 1100×850 pixels. While the CAD system 104 may be directly connected to the imaging device 102, it is also possible for the imaging device 102 to be separate from the CAD system 104 and for digital images to be transferred between the two systems by some intermediate storage device such as a portable disk (not shown).

In one embodiment of this invention, a LUMISYS Model 150 laser film digitizer is used as the digitizer 116. The scanning pixel size of the LUMISYS digitizer is selectable in the range 50×50 $\mu m^2$ to 200×200 $\mu m^2$, and the gray level of the digitization is twelve (12) bits. For the embodiments described herein, the size of the laser focal spot and scanning pixel size were set to 100×100 $\mu m^2$.

The software of the present invention, a CAD program 118, implemented on the CAD system 104, can be written in any suitable high-level computer language. In the present embodiment, the software is written in a combination of the programming languages C and C++. Further, while aspects of the present invention have been implemented in software running on a computer system as described above, all aspects of the present invention can also be implemented in hardware.

Overview of Operation of the Multi-view CAD Scheme

Figure 2:
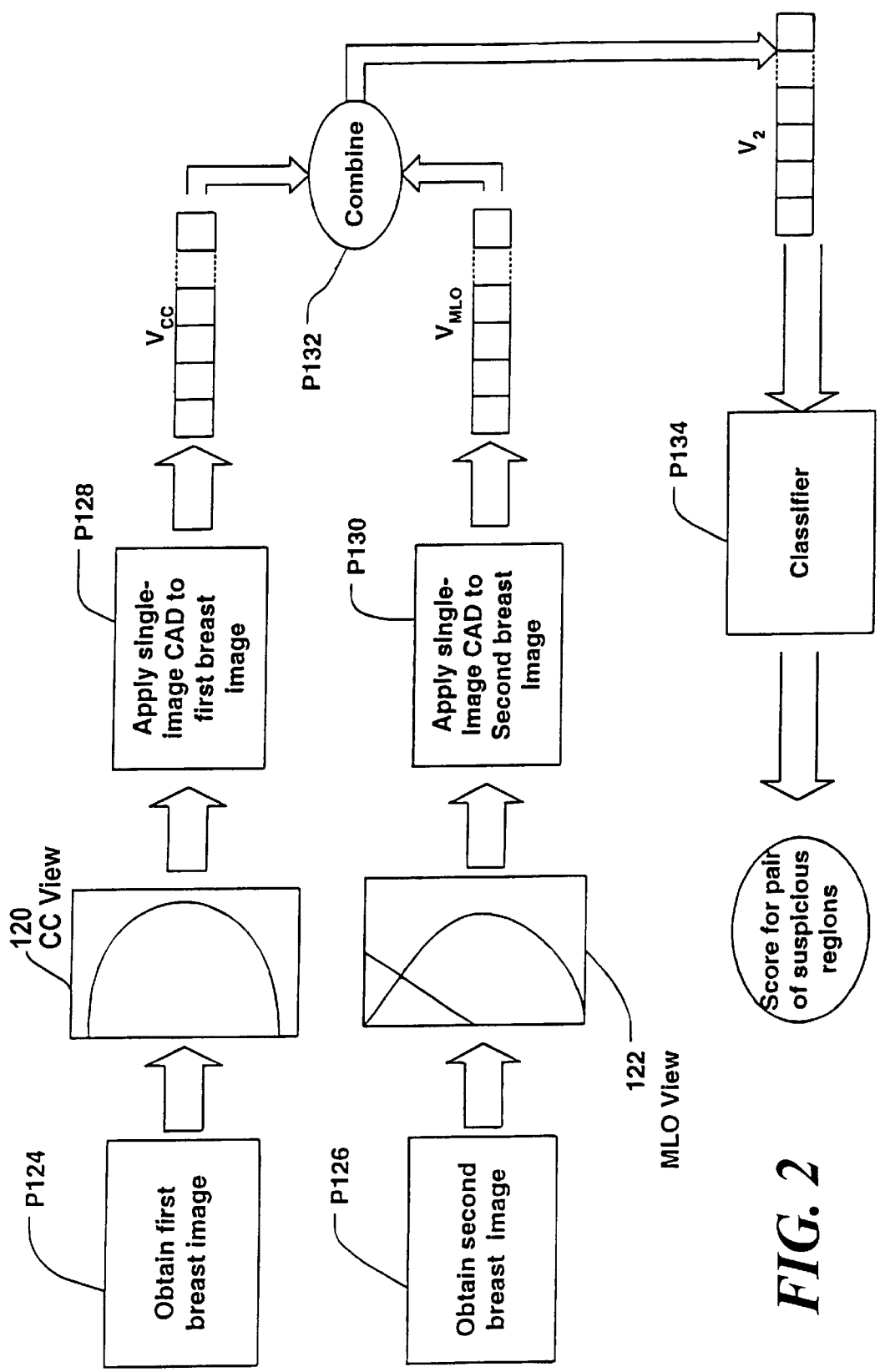
FIG. 2 is a flowchart showing operation of an embodiment of the present invention.

FIG. 2 is a flowchart showing operation of an embodiment of the present invention. For the sake of discussion, and by way only of example, the invention will be described with reference to mammographic images, although it is not intended to be limited to such images. First two images 120 and 122 are obtained (at P124, P126) of the same anatomical region, preferably a human breast. In preferred embodiments, one image 120 is from the craniocaudal (CC) view and the other image 122 is from the mediolateral oblique (MLO) view. The images are obtained using the image acquisition device 102 and the digitizer 116. The two images 120, 122 may be stored in secondary storage 110 for subsequent processing.

Next, a single-image CAD is applied (at P128, P130) to each of the two images 120, 122 in order to extract feature vectors ($V_{CC}$ and $V_{MLO}$) of various suspicious regions depicted in the images. The two images can each be processed with the same single-image CAD mechanism, or a different mechanism can be used for each image. In a preferred embodiment, a number of single-view features have been selected based on their expected relative invariance under compression of the tissue. These features have been correlated for ipsilateral projections of a mass.

All possible combinations of suspicious regions, with one from the CC view and the other from the MLO view, are evaluated. Each such pair is identified as either T (i.e., two regions which are projections of the same actual mass), or as F (i.e., a pair involving at least one false positive or a pair which consist of two true positives which are not projected from the same mass).

A two-view feature vector ($V_2$) is derived for each pair of suspicious regions by combining (at P132) the single-image feature vectors $V_{CC}$ and $V_{MLO}$, for both regions in a pair. Because the single-image features are correlated for projections of a mass (i.e., the two values should be approximately equal), a measure of the ratio of single-image feature values is used to define each multi-view feature. Specifically, single-image features are combined by taking the absolute value of the difference of their logarithms, to produce the corresponding multi-view features. That is, $V2_i=|\ln VCC_i-\ln VMLO_i|$.

A Bayesian network is trained to classify (at P134) pairs based on each individual feature as well as on the combination of all features. The combined classification provides a probability estimate for each pair.

Aspects of this invention are now described in greater detail.

Processing by single-image CAD

The methods related to this invention do not depend on the particular implementation of single-image CAD. However, in a generic sense, the single-image CAD algorithm must generate a feature vector and a score associated with each detected suspicious region. Further, it must be feasible to operate the single-image CAD algorithm at a high sensitivity, since this places limits on the maximum performance that can be achieved with the multiview techniques. Typically, the current single-image CAD algorithm identifies several suspicious regions on each view. For multi-view analysis, its classification threshold should be set at a level where sensitivity is 98%, which generates about 2.5 suspicious regions per image. For each suspicious region, a single-image feature vector is calculated and retained. The feature vector contains, among other features, the specific features needed for deriving the multi-view feature vector.

Calculation of Features

A number of single-image features have been identified that are relatively invariant under soft tissue compression, and hence, correlated for ipsilateral projections of a mass. These features include 1) radial distance of suspicious region from the nipple;
2) length of region projection parallel to the nipple axis line;
3) integrated contrast difference;
4) size of the suspicious region; and
5) measure of complexity of region boundary.

Each multi-view feature is defined to be the absolute value of the logarithm of the ratio of the corresponding single-image features, though there are other possible alternatives to this. The actual components of the multi-view feature vectors currently used are based on (1) ratio of radial distances of centers of suspicious regions from nipple;
(2) ratio of lengths of region projections parallel to the nipple axis lines;
(3) ratio of integrated contrast differences;
(4) ratio of the sizes of the suspicious regions; and
(5) ratio of measure of complexity of region boundaries.

A description of each feature follows.

Position of centers of regions

For each suspicious region detected by single-image CAD, a (two-dimensional) center-of-mass is calculated. The single-image feature is defined to be the distances between this center-of-mass and the nipple. The corresponding multi-view feature, for a pair of suspicious regions, is defined to be the absolute value of the difference of the logarithms of the two distances. These distances are shown, as R1 and R2, on the schematic representation of an ipsilateral pair of mammograms, in FIG. 3.

A common practice for mammographers is to compare the radial distance of suspicious regions from the nipple, often referred to as the "Arc" method of triangulation. If these radii are roughly the same, then the points are compatible in the sense that they could, but not necessarily must, correspond to the same tissue.

Projected length

The nipple axis line in each image is automatically identified and each suspicious region is perpendicularly projected onto this line. These projections are indicated as L1 and L2 in FIG. 3.

It is hypothesized that the change in length of a tissue volume during breast compression, in the direction perpendicular to the chest wall, does not depend appreciably on the view (i.e., the direction of compression) once a correction is made for obliqueness of image plane relative to the chest wall.

To find the nipple axis, previously reported fully automatic methods were used to segment breast tissue from the image background so as to identify the skin line, and to detect the nipple and the pectoral muscle (on MLO views). These methods are described in B. Zheng et al, "Computerized Detection of Masses From Digitized Mammograms: Comparison of single-image segmentation and bilateral image subtraction" Acad. Radiol., 1995; 2:1056–106; W. F. Good et al, "JPEG Compatible Data Compression of Mammograms," *J. Digital Imaging* 1994; 7:123–132; and G. S. Maitz et al, "Preliminary clinical evaluation of a high-resolution telemammography system," *Inves. Radiol.* 1997; 32(4):236–40, each of which is incorporated herein by reference. The chest wall is not normally visible in the CC view, so in this case we assume that the chest wall was parallel to the edge of the image. Further, it was not always possible to locate the nipple in one or the other of the views, and when this occurred, we assume a location for the nipple at the most extreme extent of the breast from the pectoral muscle. For each pair of suspicious regions, the absolute value of the logarithm of the ratio of the two projections was used to represent the two-view feature.

Integrated contrast differences

When exposure conditions are held constant and the breast contains a mass superimposed on the background in such a way that there is a detectable difference between the mass and the background, then the integrated density difference between the mass and the background, to a first-order approximation, is invariant with respect to degree of compression and view, under some very general conditions.

Figure 4:
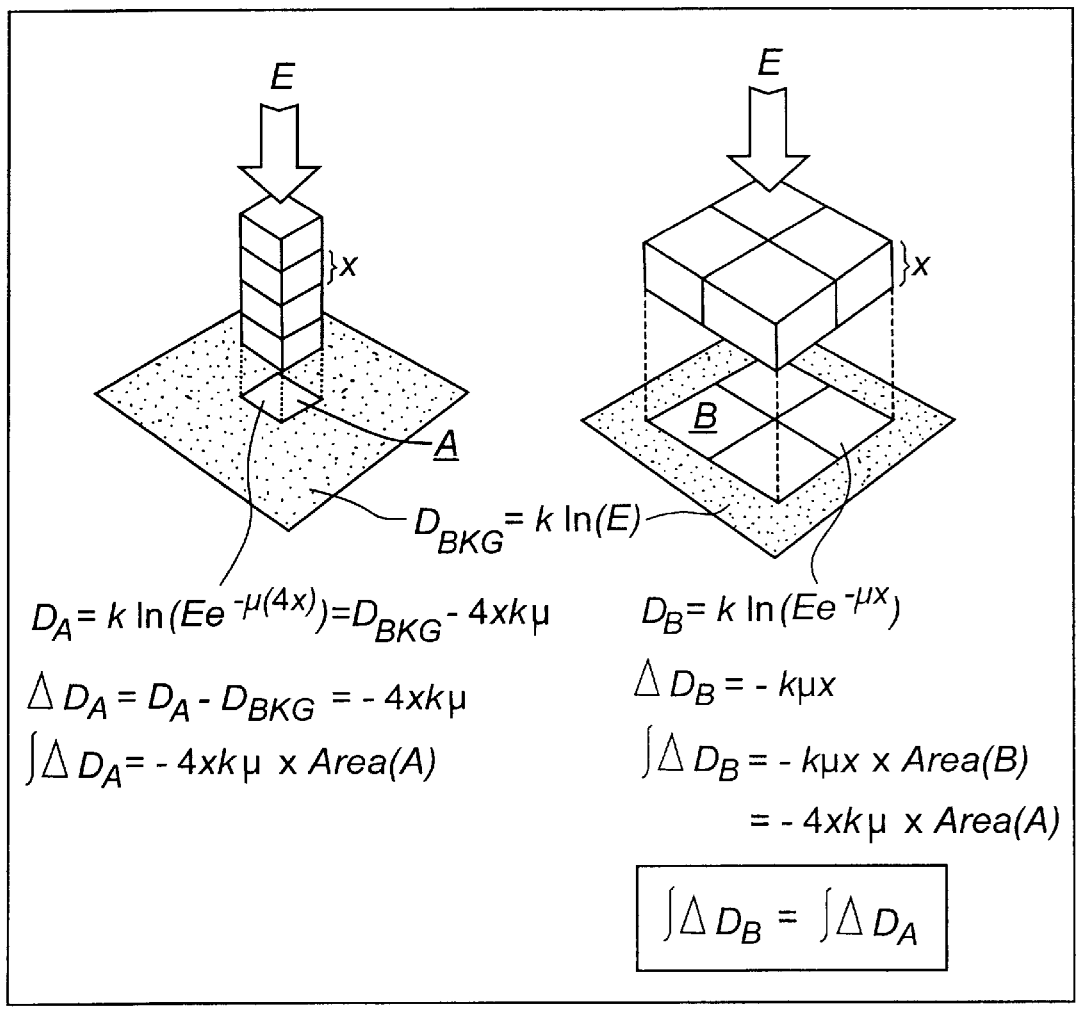
FIGS. 4 and 5 explain and depict approximation of integrated contrast differences according to embodiments of the present invention.

An explanation of this invariance is shown in FIG. 4, where each block represents a mass voxel, and it can be seen that the integrated contrast difference is independent of the way in which the voxels are stacked. The mathematical proof involves showing that the differential density resulting from a differential voxel element is independent of it placement, and integrating over all voxel elements in a mass gives the invariant density change due to the mass. Although the argument in FIG. 4 can be generalized, its accuracy is limited by the underlying assumptions, including among others, that density changes are on the linear part of the D-log-E curve, and that x-ray attenuation follows the standard exponential law.

Figure 5:
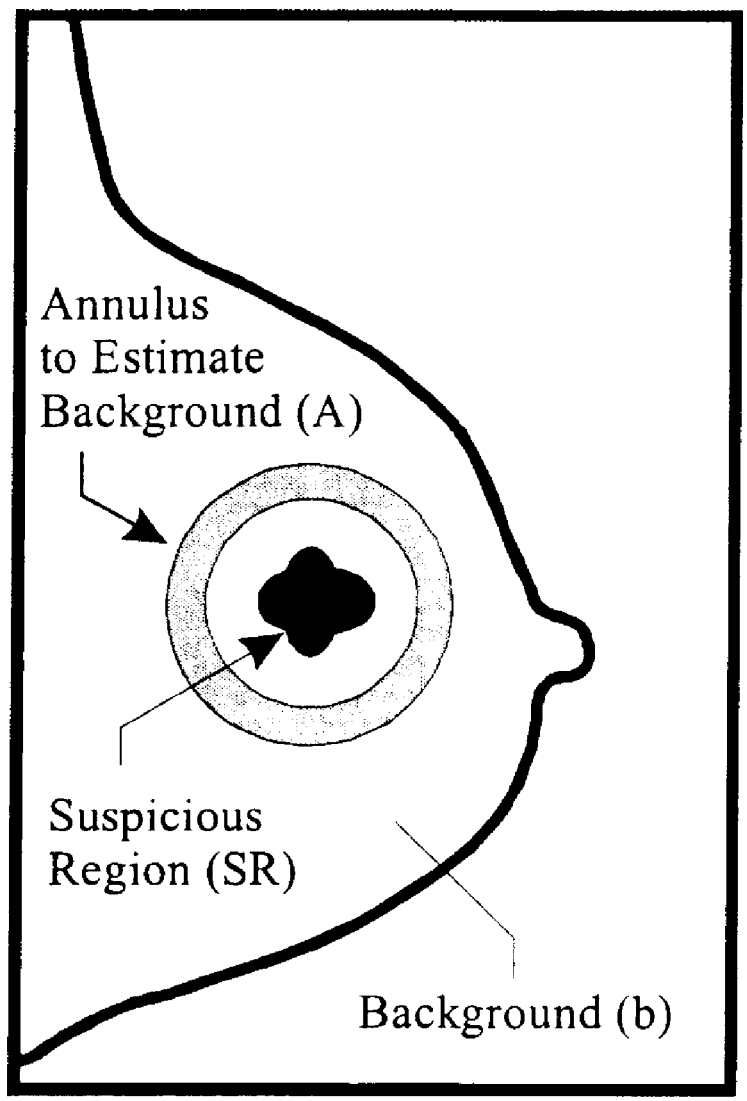
Figure 9A:
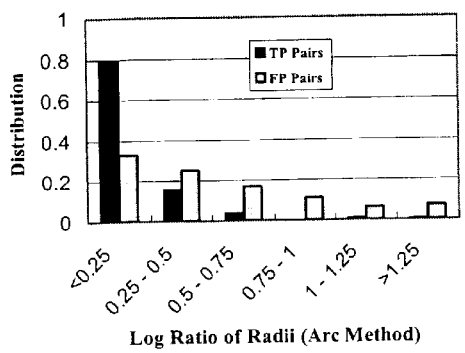
Figure 9B:
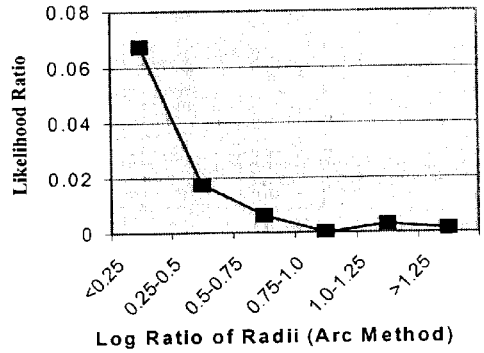
Figure 9C:
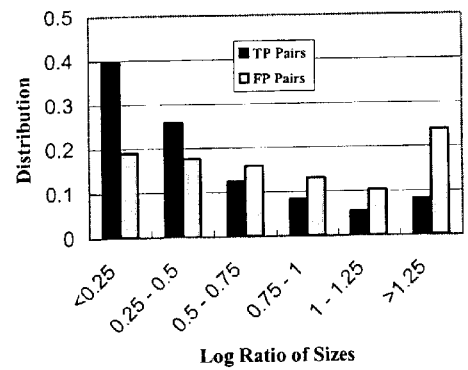
Figure 9D:
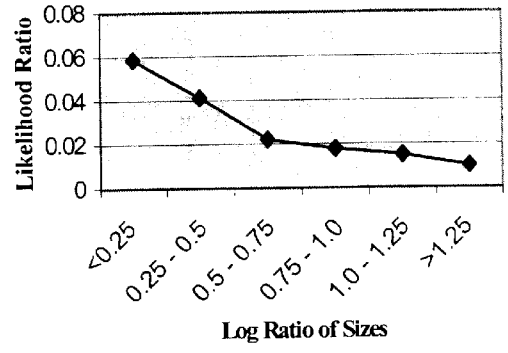
Figure 9E:
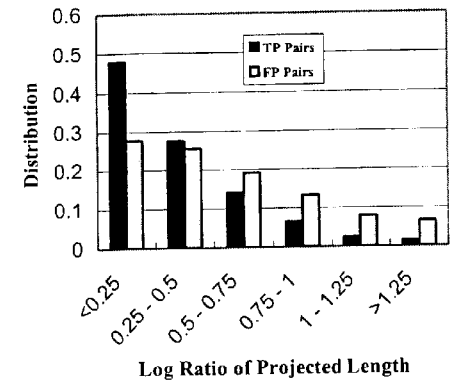
Figure 9F:
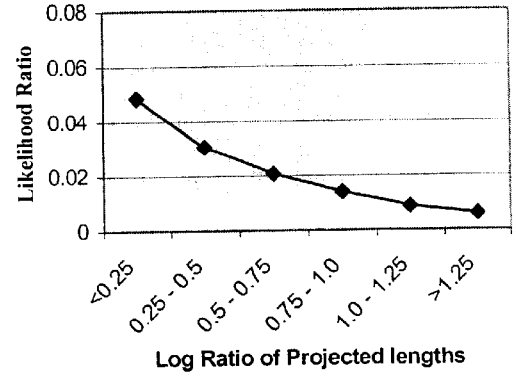
Figure 9G:
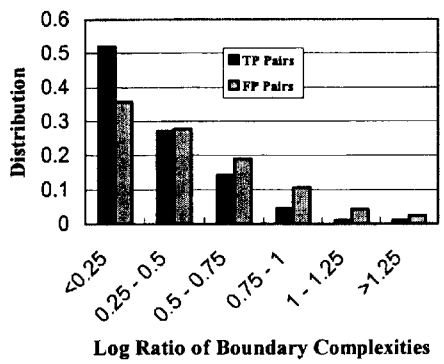
Figure 9H:
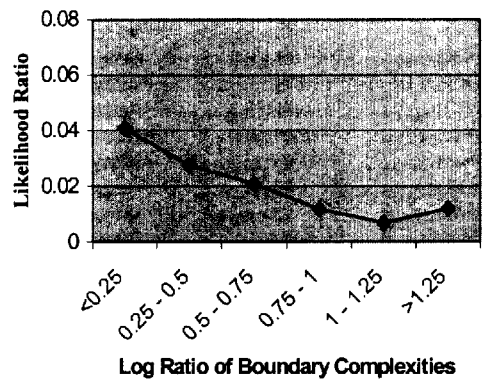
Figure 9I:
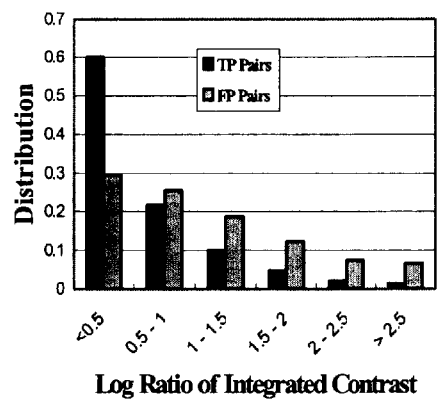
Figure 9J:
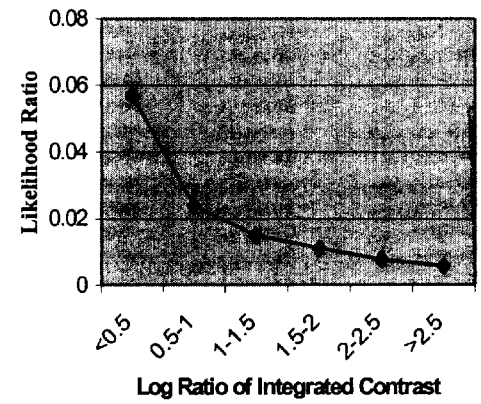

The approximation of this feature, integrated contrast differences, as shown in FIGS. 4 and 5, involves placing an annulus (A) around suspicious regions (SR) and averaging pixel values covered by the annulus to approximate the background density inside the annulus. This average value is then subtracted from each of the pixels inside the annulus and these differences are tabulated.

Thus, as shown in FIG. 4, $$D_A = k \ln(Ee^{-\mu 4x}) = D_{BKG} - 4xk\mu \quad (1)$$

where $D_A$ is defined as the density resulting from the vertical stack of four voxels, each of height x, (x is defined as the height of a voxel); $\mu$ is defined as the linear attenuation coefficient of voxels; k is a constant representing the contrast of the detector (e.g., film); and $D_{BKG}$ is defined as the density of background (fully exposed) areas of the detector.

$$\Delta D_A = D_A - D_{BKG} = -4xk\mu \quad (2)$$

$$\int \Delta D_A = -4xk\mu \times \text{Area}(A) \quad (3)$$

$$D_B = k \ln(Ee^{-\mu x}) \quad (4)$$

where $D_B$ is defined as the density resulting from a single voxel of height x.

$$\Delta D_B = -k\mu x \quad (5)$$

$$\int \Delta D_B = -k\mu x \times \text{Area}(B) = -4xk\mu \times \text{Area}(A) \quad (6)$$

$$\int \Delta D_B = \int \Delta D_A \quad (7)$$

As shown in FIG. 5, $$\text{Integrated Contrast} = \sum_{SR}(SR_{ij} - b_{ij})) \quad (8)$$

$$\approx \sum_{SR}(SR_{ij} - B \times area(SR))$$

-continued $$\text{where } B = \frac{1}{area(A)} \sum_A b_{ij}$$

To derive the corresponding two-view feature, subtract the logarithms of the two single-view values.

Relative sizes of the suspicious regions

The size of a suspicious region is the number of pixels covered by its projection. (This value should be strongly correlated to the projected length feature defined above.)

Relative complexity of region boundary

If a mass is spiculated in one view then it should be spiculated in the other view as well. This will generally be the case for masses that are essentially isotropic. A measure, sometimes referred to as compactness, is used for the complexity. The measure is defined to be the square of the perimeter of a suspicious region divided by its area.

Product of single-image probabilities

The single-image CAD algorithm employed provides a score that is an estimate of the probability that a suspicious region is the projection of an actual mass. The product of the two scores, or some other function of the scores, for a pair of regions can be an effective measure of whether both regions are real, but not necessarily of whether they correspond to each other.

Other features

Other useful features have been identified, including, but not limited to, measures of texture and measures of the margin definition of masses.

The classification mechanism 134 for combining the features corresponding to a pair of suspicious regions can be any traditional classification procedure such as neural networks, Bayesian networks, KNN, or a direct estimation of the multidimensional probability density function. A presently preferred embodiment uses a Bayesian network, which was trained and tested on a preliminary dataset, using a jackknifing process, to classify pairs of suspicious regions as either T or F. The jackknifing process involves leaving out one case at a time and using the remaining cases to calculate the conditional probabilities required by the Bayesian network. The case that was withheld is then classified by the network, and the process is repeated until each case has been classified once. The output node of the Bayesian network produces a value that reflects the likelihood that the two regions in a pair correspond to projections of the same actual mass.

Multi-view summary score for breast

There are various ways of combining the scores associated with pairs of suspicious region, to produce a summary score for a breast. The simplest is to take either the maximum or sum of scores over all pairs. Alternately, if it is assumed that the score parameters are actually proportional to true probabilities, and that they are independent or their dependence can be characterized, then they can be combined using conventional probability techniques. In any event, the combined score will be the parameter used for classifying the breast as negative or positive for the presence of a mass.

To improve single-image CAD performance, the results of the multi-view CAD analysis are projected back to the single-image CAD algorithm. For each suspicious region in the original views, a value can be assigned which is derived from the output score of the Bayesian network over all pairs that include the particular region. This new parameter, which depends predominately on multi-view features, is passed back and inserted into the single-image feature vector for the region so that this information can be considered in a second, and possibly more accurate, classification process by the single-image CAD algorithm. In effect, the parameter being passed back for each suspicious region indicates the likelihood that the suspicious region was confirmed on the opposing view.

Single-image CAD provides a score for each detected suspicious region. For each pair of suspicious regions, with one from the CC view and the other from the MLO view, there is a pair of scores that can be combined to provide a score for the pair. If the single-image scores are independent probabilities, then the product of the two scores is a probability score for the pair. If the scores are not probabilities, they can be combined with any of the standard classification techniques, such as neural networks, Bayesian networks, or direct estimation of the joint probability density function. The scores for all such pairs can be combined to form a score for the breast. The two mechanisms for doing this that we have developed are to take the maximum or sum over all pairs.

Example

The process according to an embodiment of this invention was applied to a set of one hundred (100) ipsilateral mammographic studies. For the resulting three hundred and ninety six (396) pairs of suspicious regions, six multi-view features were defined and evaluated. Histograms indicating the distributions for each feature were calculated to detect any difference between the distributions for T and F pairs. A Bayesian network was trained and tested, using a jackknifing process, to classify pairs of regions as either T or F.

Cases used in study

The image dataset consisted of one hundred (100) pairs of ipsilateral views taken on women having screening or diagnostic mammograms in 1995 at Magee Womens Hospital's Breast Care Centers, or Montefiore Hospital, both in Pittsburgh, Pa. Only MLO and CC views were used. These are the views customarily performed in the screening environment. Cases were only used if complete follow-up documentation was available. The verification of positive cases consisted of biopsy and/or surgical reports, while establishing a case as being negative required a negative follow-up for at least a two-year period. This set of cases included 38 verified masses. The protocol followed in selecting mammography cases is described in K. M. Harris et al, "Exploring Computerized Mammographic Reporting With Feedback," *PROC SPIE*, (1993), 1899:46–52, which is incorporated herein by reference. Films were digitized using a laser film digitizer (Lumisys, Inc., Sunnyvale, Calif.), at 12 bits with 100 $\mu$m pixel size, which produced an array of approximately 1.8K×2.4K, and were reduced to an effective resolution of 400 $\mu$m by digital filtration, to maintain compatibility with the single-image CAD algorithms.

Processing by single-image CAD

The particular single-image CAD algorithm employed in the study utilized single-image segmentation in conjunction with a multi-layer topographic approach. This method, and its initial results on different data sets, is described in B. Zheng et al, "Computerized Detection of Masses From Digitized Mammograms: Comparison Of Single-Image Segmentation And Bilateral Image Subtraction" *Acad. Radiol.,* 1995; 2:1056–106; and Zheng et al, "A Method For Computer-Aided Detection Of Clustered Microcalcifications In Digitized Mammograms," *Academic Radiology* 1995; 2:655–662, both of which are incorporated herein by reference. Typically, this CAD algorithm identifies several suspicious regions on each view. For this study, the classification threshold was set at a level where sensitivity was 98%, which generated an average of two suspicious regions per image.

Except for the feature related to single-image probabilities, each multi-view feature was defined to be the absolute value of the logarithm of the ratio of the corresponding single-view features. The actual components of the multi-view feature vectors were based on (1) A ratio of radial distances of centers of suspicious regions from nipple;
(2) A ratio of lengths of region projections parallel to the nipple axis lines;
(3) A ratio of integrated contrast differences;
(4) A ratio of the sizes of the suspicious regions;
(5) A ratio of measure of complexity of region boundaries; and
(6) A product of single-image probabilities.

Figure 3:
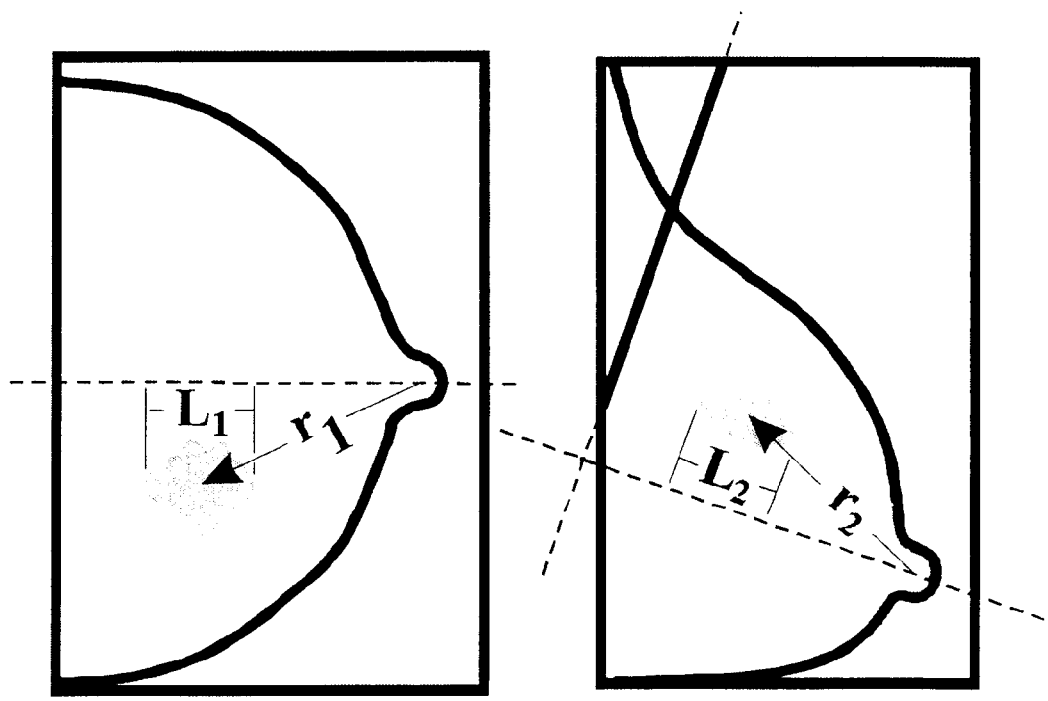
FIG. 3 is a schematic representation of an ipsilateral pair of mammograms used to describe aspects of embodiments of this invention.

FIG. 3 shows how the radial distance from the nipple and the projected length single-image measures are defined. The method of calculating integrated contrast is represented in FIG. 5, where the average of pixel values over an annulus surrounding a suspicious region is used to estimate the image background, and the difference between this background and pixels corresponding to the mass is integrated over the area of the mass. This result should be relatively invariant with respect to projection. For the boundary complexity feature, the square of the perimeter of a region was divided by its area, sometimes referred to as compactness.

In addition to deriving a score for each pair of densities, single-image and multi-view summary scores were calculated for breasts. The single-view CAD score for each breast was obtained by combining the individual results for each image (i.e., the maximum probability of a suspicious region in either image), while the multi-view score for a breast was the maximum probability taken over all pairs.

Results

FIG. 6A is the distribution of single-image radial distances from the nipple for T and F densities. It can be seen that the two distributions are very similar and present little opportunity for use in distinguishing between T and F regions. In contrast, the distributions of the multi-view feature based on these radii (i.e., difference of their logarithms) are very different for T and F regions, as shown in FIG. 6B. This indicates that there is information related to this feature in pairs of images that cannot be extracted by analyzing the individual images independently. FIG. 7 includes the receiver operating characteristic (ROC) curve for this feature.

Histograms indicating the distributions and likelihood ratios for the features are shown in FIGS. 9A–9J. In these charts, the black bars in each group represent T pairs and the gray bars represent F pairs, either true positives combined with false positives, two false positives, or a two true positives, which are not the projection of the same mass. It is clear from the figures that, for all of these features, there is a significant difference in the distribution between the T and the F pairs. That is, distributions for all six multi-view features were significantly different for T versus F pairs. The least significant of the differences was the measure of relative complexity of region boundaries. The performance of individual features is summarized in Table 1. All of the Az values are significantly greater than 0.5 indicating that each of these features provides useful information for classifying pairs. Combined performance of the Bayesian network indicates a significant ability to distinguish between T pairs and F pairs (Az=0.84±0.03), using predominately the information that is attributed to the multi-view content.

Figure 10:
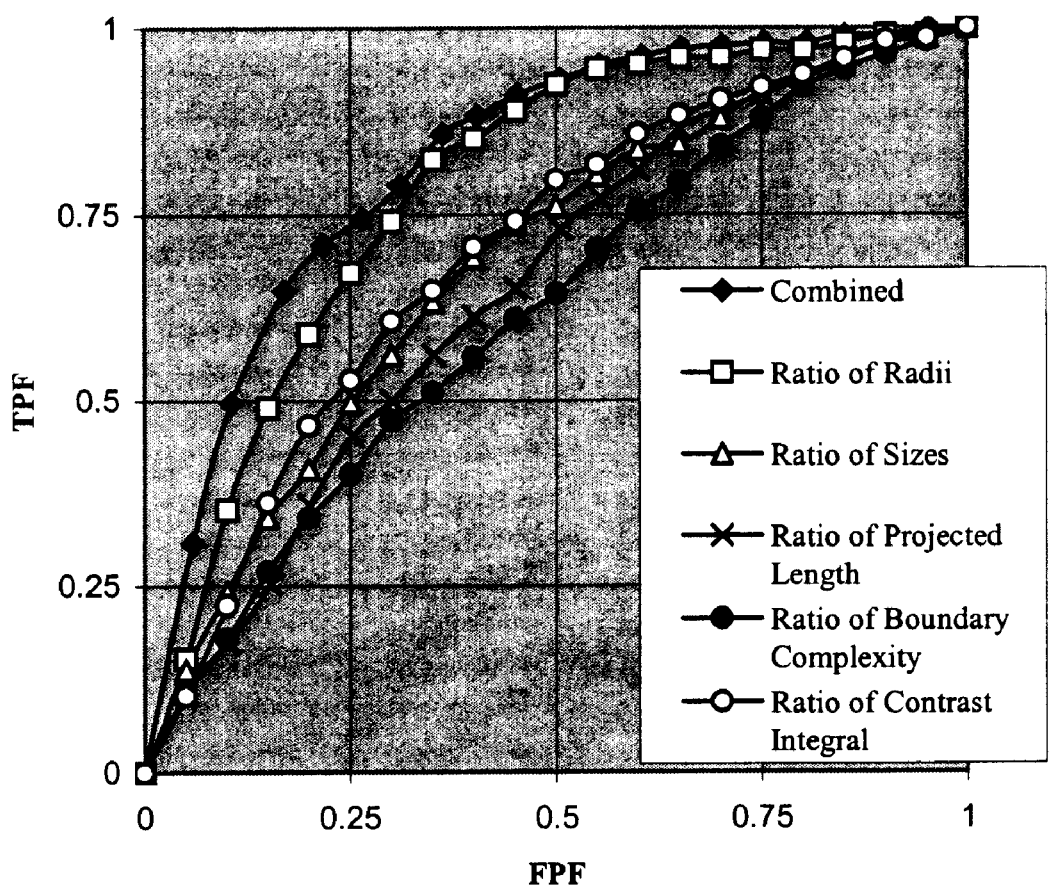

The ROC curve for all features combined is given in FIG. 10. The per breast result for multi-view CAD was significantly higher than the result from-single-image CAD.

TABLE I

Performance of Individual Features

| Feature | Az |
| --- | --- |
| Ratio of radii | 0.79 |
| Contrast Integral | 0.70 |
| Ratio of Sizes | 0.68 |
| Ratio of Projected Length | 0.65 |
| Ratio of Boundary Complexities | 0.62 |
| All combined | 0.82 |

Features for this study were chosen based on an intuitive expectation that they would be relatively invariant, and no effort was made to optimize either the feature set or individual features.

Dependence on single-view CAD

To achieve a high sensitivity in multi-view CAD, the single-view algorithm must be operated at high sensitivity. But because the number of pairs that must be evaluated in the multi-view analysis increases roughly as the square of the average number of suspicious regions per image reported by single-view CAD, the performance of multi-view CAD, as currently implemented, depends on the underlying false positive rate of single-view CAD. Using single-view CAD at an operating point that provides about two suspicious regions per image, seems to be a reasonable compromise.

While the above method and system have been described for the detection of masses and microcalcifications in mammograms, it will be appreciated that the present invention can be used for different types of applications and for different types of exams. For example, the present invention can be used for detecting nodules in chest x-rays, masses in computed tomography of the liver and the like.

In addition, while the invention has been described with reference to images produced by the same imaging device, it will be appreciated that the present invention can use different imaging devices and/or techniques to produce the pairs of images. Thus, for example, radiographs and ultrasound images may be combined according to the present invention.

While the invention has been described with reference to two images of the same anatomical region, it will be appreciated that the present invention can use multiple images produced by the same or different imaging mechanisms.

Although described with reference to a particular system, the present invention operates on any computer system and can be implemented in software, hardware or any combination thereof. When implemented fully or partially in software, the invention can reside, permanently or temporarily, on any memory or storage medium, including but not limited to a RAM, a ROM, a disk, an ASIC, a PROM and the like.

Thus, methods, systems and devices for detecting abnormal regions in living tissue are provided. One skilled in the art will appreciate that the present invention can be practiced by other than the described embodiments, which are presented for purposes of illustration and not limitation, and the present invention is limited only by the claims that follow.

We claim:

1. A method of detecting an abnormal region in living tissue, the method comprising:

obtaining images from different views of the living tissue;

performing single-image CAD of each image to determine suspected abnormal regions depicted in the image; and combining measurements of the suspected abnormal regions in each image to determine whether a suspected abnormal region is an abnormal region.

2. The method as in claim 1, wherein the living tissue is a human breast, wherein the abnormal region is a mass in the breast, and wherein the obtaining images comprises obtaining ipsilateral mammographic views of the breast.

3. The method as in claim 2, wherein one image is from a craniocaudal view of the breast and the other image is from the mediolateral oblique view of the breast.

4. The method as in claim 2, wherein the performing of the single-image CAD of each image produces a feature vector for each various suspicious regions depicted in the images.

5. The method as in claim 4, wherein the features are relatively invariant or behave predictably with respect to breast compression.

6. The method as in claim 4, wherein the features include one or more of
- a radial distance of the suspicious region from the nipple;
- a length of region projection parallel to the nipple axis line;
- an integrated contrast difference;
- a size of the suspicious region;
- a measure of complexity of the region boundary;
- a measure of image texture within the region; and
- a measure of definition of region boundary.

7. The method as in claim 2, wherein the performing of the single-image CAD of each image produces a measure of likelihood that a suspected abnormal region is an abnormal region.

8. The method as in claim 2, wherein the combining of measurements comprises:
- evaluating combinations of suspected abnormal regions from each view; and
- producing a single multi-view measurement for each suspected abnormal region based on the measurements of corresponding regions from each view.

9. A method as in claim 8, wherein each multi-view feature is defined to be the absolute value of the logarithm of the ratio of the corresponding single-image features.

10. The method as in claim 8, wherein the multi-view measurement for each suspected abnormal region is based on a combination of the corresponding single-view measurements.

11. The method as in claim 8, wherein the single multi-view measurement for each suspected abnormal region is based on a combination of the various single-view measurements for the region.

12. The method as in claim 11, wherein the combination is obtained with a statistical classification mechanism from the group of a neural network, Bayesian network, KNN algorithm or by estimating the probability density function.

13. The method as in claim 1, further comprising:
using the result of the combining to train the single-image CAD.

14. The method as in claim 1, further comprising:
combining the multi-view measurements from the various suspected abnormal regions to obtain a multi-view measurement for the breast as a whole.

15. A method of detecting a mass in a human breast, the method comprising:
obtaining ipsilateral mammographic views of the breast;
for each image, performing CAD of the image to determine suspected masses depicted in the image; and
combining measurements of the suspected masses in each image to determine whether a suspected abnormal region is a mass.

16. The method as in claim 15, wherein one image is from a craniocaudal view of the breast and the other image is from the mediolateral oblique view of the breast.

17. The method as in claim 15, wherein the performing of the CAD of each image produces a feature vector for each various suspicious regions depicted in the images.

18. The method as in claim 17, wherein the features are relatively invariant or behave predictably with respect to breast compression.

19. The method as in claim 18, wherein the features include one or more of
- a radial distance of the suspicious region from the nipple;
- a length of region projection parallel to the nipple axis line;
- an integrated contrast difference;
- a size of the suspicious region;
- a measure of complexity of the region boundary;
- a measure of image texture within the region; and
- a measure of definition of region boundary.

20. The method as in claim 15, wherein the performing of the single-image CAD of each image produces a measure of likelihood that a suspected abnormal region is an abnormal region.

21. A method as in claim 15, wherein the combining of measurements comprises:
- evaluating combinations of suspected abnormal regions from each view; and
- producing a single multi-view measurement for each suspected abnormal region based on the measurements of each region from each view.

22. A method as in claim 21, wherein each multi-view feature is defined to be the absolute value of the logarithm of the ratio of the corresponding single-image features.

23. A method as in claim 21, wherein the multi-view measurement for each suspected abnormal region is based on a combination of the corresponding single-view measurements.

24. A method as in claim 21, wherein the multi-view measurement for each suspected abnormal region is based on a combination of the various single-view measurements for the region.

25. A method as in claim 24, wherein the combination is obtained with a statistical classification mechanism from the group of a neural network, Bayesian network, KNN algorithm or by estimating the probability density function.

26. The method as in claim 15, further comprising:
combining the multi-view measurements from the various suspected abnormal regions to obtain a multi-view measurement for the breast as a whole.

27. An apparatus of detecting an abnormal region in living tissue, the apparatus comprising:
- a mechanism constructed and adapted to obtain images from different views of the living tissue;
- a mechanism constructed and adapted to perform single-image CAD of each image to determine suspected abnormal regions depicted in the image; and
- a mechanism constructed and adapted to combine measurements of the suspected abnormal regions in each image to determine whether a suspected abnormal region is an abnormal region.

28. The apparatus as in claim 27, wherein the living tissue is a human breast and wherein the abnormal region is a mass in the breast, and wherein the obtaining mechanism comprises a mechanism constructed and adapted to obtain ipsilateral mammographic views of the breast.

29. The apparatus as in claim 28, wherein one image is from a craniocaudal view of the breast and the other image is from the mediolateral oblique view of the breast.

30. The apparatus as in claim 29, wherein the performing mechanism is constructed and adapted to produce a feature vector for each various suspicious regions depicted in the images.

31. The apparatus as in claim 30, wherein the features are relatively invariant or behave predictably with respect to breast compression.

32. The apparatus as in claim 30, wherein the features include one or more of:
   a radial distance of the suspicious region from the nipple;
   a length of region projection parallel to the nipple axis line;
   an integrated contrast difference;
   a size of the suspicious region;
   a measure of complexity of the region boundary;
   a measure of image texture within the region; and
   a measure of definition of region boundary.

33. The apparatus as in claim 28, wherein the performing of the single-image CAD of each image produces a measure of likelihood that a suspected abnormal region is an abnormal region.

34. The apparatus as in claim 28, wherein the mechanism for combining of measurements comprises:
   a mechanism constructed and adapted to evaluate combinations of suspected abnormal regions from each view; and
   a mechanism constructed and adapted to produce a single multi-view measurement for each suspected abnormal region based on the measurements of corresponding regions from each view.

35. The apparatus as in claim 34, wherein each multi-view feature is defined to be the absolute value of the logarithm of the ratio of the corresponding single-image features.

36. The apparatus as in claim 34, wherein the multi-view measurment for each suspected abnormal region is based on a combination of the corresponding single-view measurements.

37. The apparatus as in claim 34, wherein the single multi-view measurement for each suspected abnormal region is based on a combination of the various single-view measurement for the region.

38. The apparatus as in claim 37, wherein the combination is obtained with a statistical classification mechanism from the group of a neural network, Bayesian network, KNN algorithm or by estimating the probability density function.

39. The apparatus as in claim 27, further comprising:
   a mechanism constructed and adapted to use the result of the combining to train the single-image CAD.

40. An apparatus as in claim 27, further comprising:
   combining the multi-view measurement from the various suspected abnormal regions to obtain a multi-view measurement for the breast as a whole.

41. An apparatus of detecting a mass in a human breast, the apparatus comprising:
   a mechanism constructed and adapted to obtain ipsilateral mammographic views of the breast;
   mechanisms constructed and adapted to, for each image, perform computer-assisted diagnosis (CAD) of the image to determine suspected masses depicted in the image;
   a mechanism constructed and adapted to combine measurements of the suspected masses in each image to determine whether a suspected abnormal region is a mass.

42. The apparatus as in claim 41, wherein one image is from a craniocaudal view of the breast and the other image is from the mediolateral oblique view of the breast.

43. The apparatus as in claim 41, wherein the CAD of each image produces a feature vector for each various suspicious regions depicted in the images.

44. The apparatus as in claim 43, wherein the features are relatively invariant or behave predictably with respect to breast compression.

45. The apparatus as in claim 43, wherein the features include one or more of
   a radial distance of the suspicious region from the nipple;
   a length of region projection parallel to the nipple axis line;
   an integrated contrast difference;
   a size of the suspicious region;
   a measure of complexity of the region boundary;
   a measure of image texture within the region; and
   a measure of definition of region boundary.

46. The apparatus as in claim 41, wherein the performing of the single-image CAD of each image produces a measure of likelihood that a suspected abnormal region is an abnormal region.

47. The apparatus as in claim 41, wherein the mechanism for combining of measurements comprises:
   a mechanism constructed and adapted to evaluate combinations of suspected abnormal regions from each view; and
   a mechanism constructed and adapted to produce a single multi-view measurement for each suspected abnormal region based on the measurements of corresponding regions from each view.

48. An apparatus as in claim 47, wherein each multi-view feature is defined to be the absolute value of the logarithm of the ratio of the corresponding single-image features.

49. An apparatus as in claim 47, wherein the multi-view likelihood for each suspected abnormal region is based on a combination of the corresponding single-view likelihoods.

50. The apparatus as in claim 47, wherein the single multi-view measurement for each suspected abnormal region is based on a combination of the various single-view measurement for the region.

51. The apparatus as in claim 50, wherein the combination is obtained with a statistical classification mechanism from the group of a neural network, Bayesian network, KNN algorithm or by estimating the probability density function.

52. The apparatus as in claim 41, further comprising:
   combining the multi-view measurements from the various suspected abnormal regions to obtain a multi-view measurement for the breast as a whole.

* * * * *